(12) United States Patent
Murdock et al.

(10) Patent No.: US 7,789,742 B1
(45) Date of Patent: Sep. 7, 2010

(54) SMART GOLF CLUB MULTIPLAYER SYSTEM FOR THE INTERNET

(75) Inventors: Wilbert Quinc Murdock, Bronx, NY (US); Robert Pollock, Jamaica, NY (US); Mohamed Aboshihata, Brooklyn, NY (US); Philip A. Williams, Salt Point, NY (US)

(73) Assignee: Wilbert Q. Murdock, Bronx, NY (US)

( * ) Notice: Subject to any disclaimer, the term of this patent is extended or adjusted under 35 U.S.C. 154(b) by 0 days.

(21) Appl. No.: 09/570,233

(22) Filed: May 12, 2000

Related U.S. Application Data

(60) Provisional application No. 60/133,722, filed on May 12, 1999.

(51) Int. Cl.
  *A63F 9/24* (2006.01)
  *A63F 7/20* (2006.01)
  *A63B 57/00* (2006.01)
  *A63B 67/02* (2006.01)
  *A63B 67/14* (2006.01)

(52) U.S. Cl. .................. 463/3; 463/2; 463/42; 473/131; 473/151; 473/219; 273/108; 273/317.2

(58) Field of Classification Search ......... 473/220–221, 473/225, 282, 285, 313, 324, 340, 351, 406, 473/131, 151, 219; 273/317.2, 108.2, 108; 463/40–42, 2–3
See application file for complete search history.

(56) References Cited

U.S. PATENT DOCUMENTS

| | | | |
|---|---|---|---|
| 4,898,389 A | | 2/1990 | Plutt |
| 5,056,783 A | * | 10/1991 | Matcovich et al. .......... 473/453 |
| 5,087,047 A | * | 2/1992 | McConnell ............. 273/183 B |
| 5,169,151 A | | 12/1992 | Conley |
| 5,209,483 A | * | 5/1993 | Gedney et al. .............. 473/223 |
| 5,365,799 A | * | 11/1994 | Okada ................... 73/862.041 |
| 5,374,063 A | | 12/1994 | Ogden |
| 5,395,116 A | | 3/1995 | Blaakman |
| 5,435,561 A | | 7/1995 | Conley |

(Continued)

OTHER PUBLICATIONS

Microsoft computer dictionary Fifth Edition, Microsoft press © 2002 $5^{th}$ —ed p. 45.*

(Continued)

*Primary Examiner*—Dmitry Suhol
*Assistant Examiner*—Robert Mosser

(57) ABSTRACT

A system that wirelessly integrates actual golf equipment with a computer and the internet to allow players remotely located from one another to play a competitive simulated game of golf. An individual player may opt to play solo or practice to improve basic golfing techniques. The system includes smart golf clubs, a golf ball receptacle and a golf club motion sensing device, all containing circuits and contact or motion sensors coupled with signal processing and radio frequency transmitter circuitry, thereby wirelessly communicate game performance information to a remote receiver-computer. The computer displays player information and visually simulates and controls a golf game between two players, via the internet, having similar equipment and remotely located from each other. Standard golf clubs may be retrofitted with the sensors and associated circuitry to convert such clubs into "smart clubs" for use with the system. The system employs specially developed computer software to process player performance data, control game play, communicate game information between players, generate and control visual simulations and display player performance information.

20 Claims, 14 Drawing Sheets

U.S. PATENT DOCUMENTS

| | | | | |
|---|---|---|---|---|
| 5,472,205 | A | * | 12/1995 | Bouton ....................... 473/225 |
| 5,616,832 | A | | 4/1997 | Nauck |
| 5,697,791 | A | * | 12/1997 | Nashner et al. ............. 434/247 |
| 5,707,298 | A | | 1/1998 | Chovanes |
| 5,709,610 | A | | 1/1998 | Ognajanovic |
| 5,779,549 | A | * | 7/1998 | Walker et al. ................. 463/42 |
| 5,779,555 | A | * | 7/1998 | Nomura et al. ............. 473/223 |
| 5,826,578 | A | * | 10/1998 | Curchod ..................... 128/782 |
| 5,826,874 | A | * | 10/1998 | Teitell et al. ................ 473/225 |
| 5,830,069 | A | * | 11/1998 | Soltesz et al. ................. 463/42 |
| 5,830,077 | A | | 11/1998 | Yavitz |
| 5,884,913 | A | * | 3/1999 | Cohen ........................ 473/154 |
| 5,964,660 | A | * | 10/1999 | James et al. ..................... 463/1 |
| 5,997,406 | A | * | 12/1999 | Selton ........................ 473/180 |
| 6,073,086 | A | * | 6/2000 | Marinelli .................... 702/141 |
| 6,179,713 | B1 | * | 1/2001 | James et al. .................. 463/42 |
| 6,254,492 | B1 | * | 7/2001 | Taggett ....................... 473/219 |

OTHER PUBLICATIONS

R.C. Johnson, Golfers Ace Net with Smart Club, Nov. 18, 1998, TechWeb, The IT Network. (web publication at http://www.techweb.com/wire/story/TWB19981118S0004).

R. Colin Johnson, 'Smart' club puts duffers in global competition on the Web, Dec. 30, 1998, (web publication at http://www.eetimes.com/story/eezine/OEG19981117S0035).

B. Santo, Product is hit or miss, Feb. 3, 1992, Electronic Engineering Times.

D. Gonzalez, If Only, an Inventor Says, He Could Invent Capital, Mar. 19, 1992, New York Times.

In search of the sweet spot, Oct. 1992, Golf Digest, pp. 14-15.

N. Graves, Hacker's Drive for Green, Sep. 9, 1996, New York Post.

"Speaking of golf . . . ", Electronic Engineering Times-Yakitori, by David Lammers, published prior to priority date claimed of May 12, 1999.

* cited by examiner

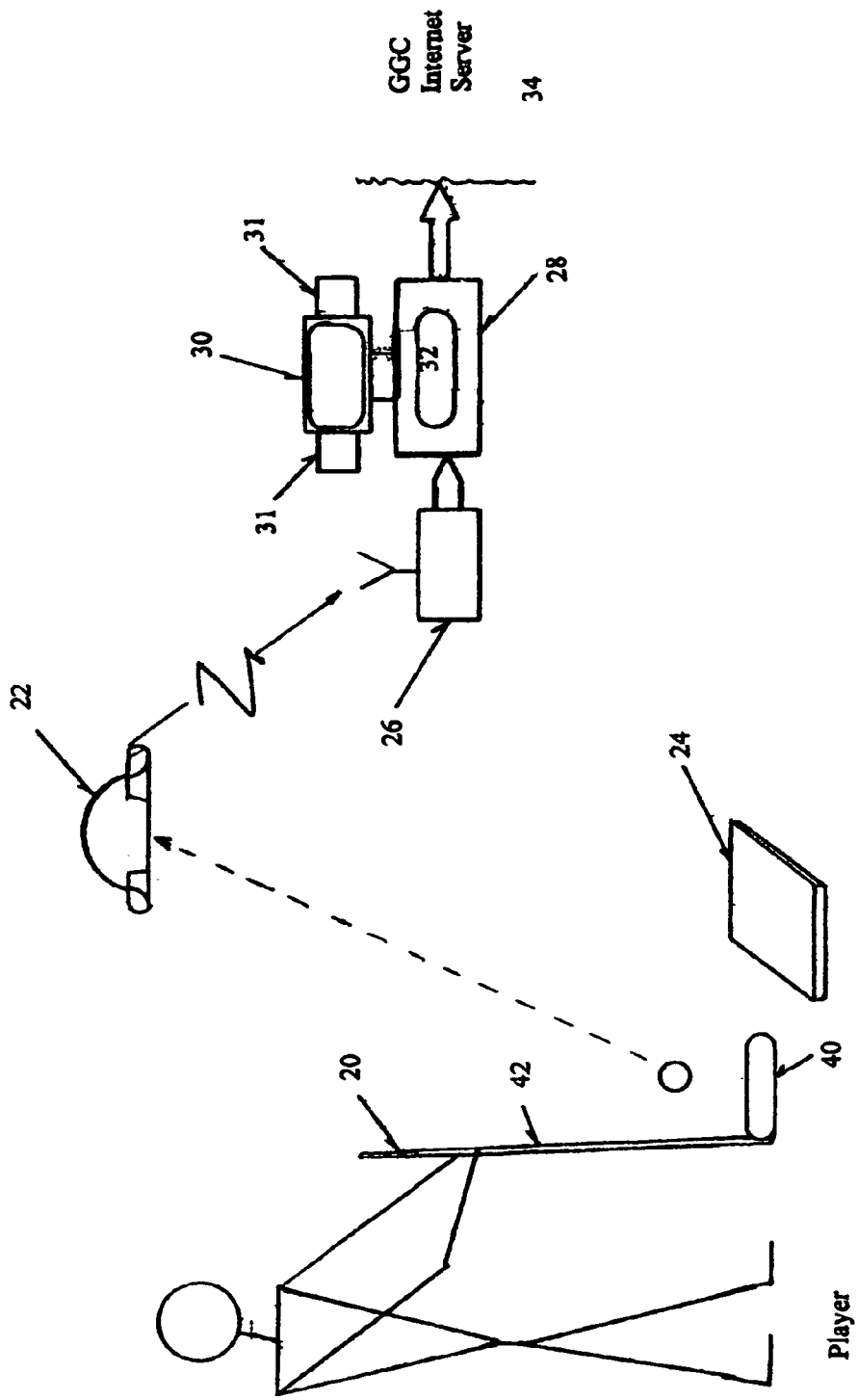
FIGURE: 1

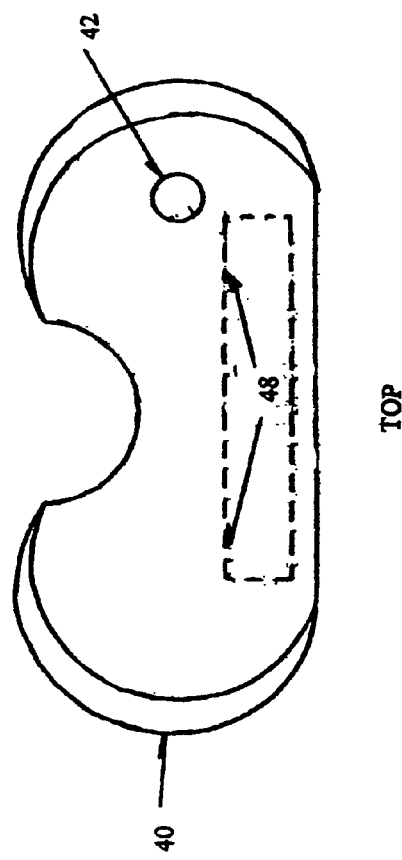
FIGURE: 2
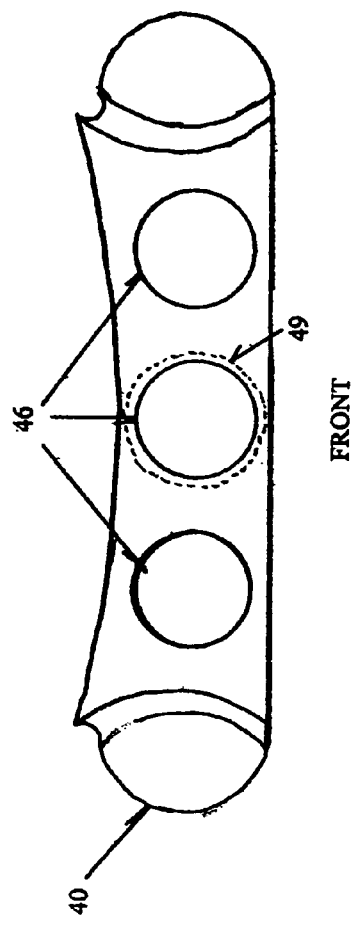
FIGURE: 3

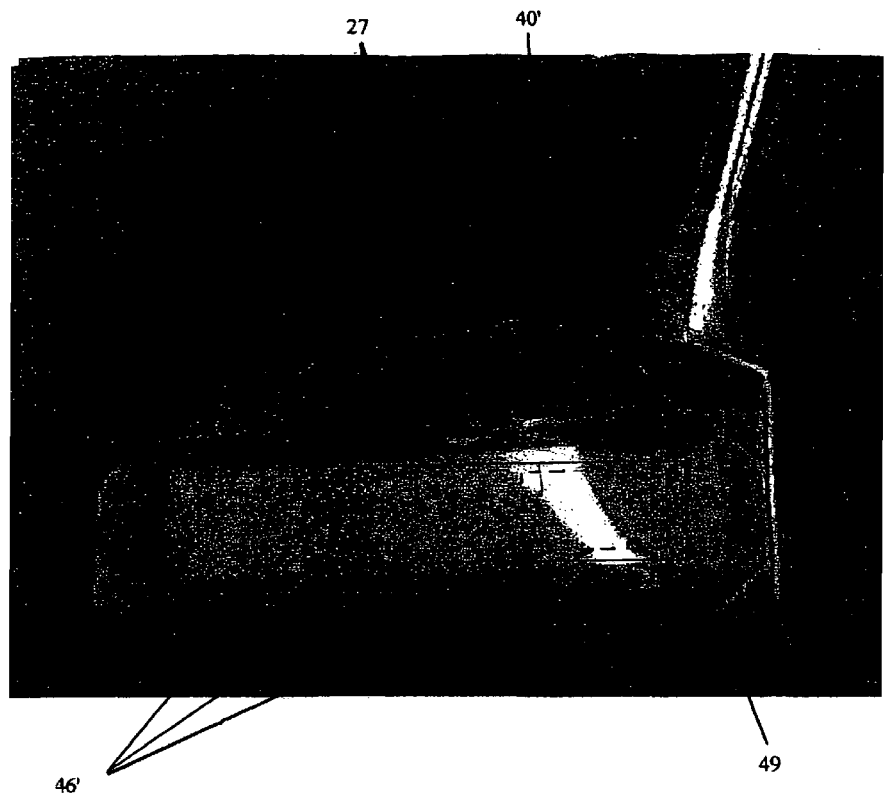
FIGURE: 3A

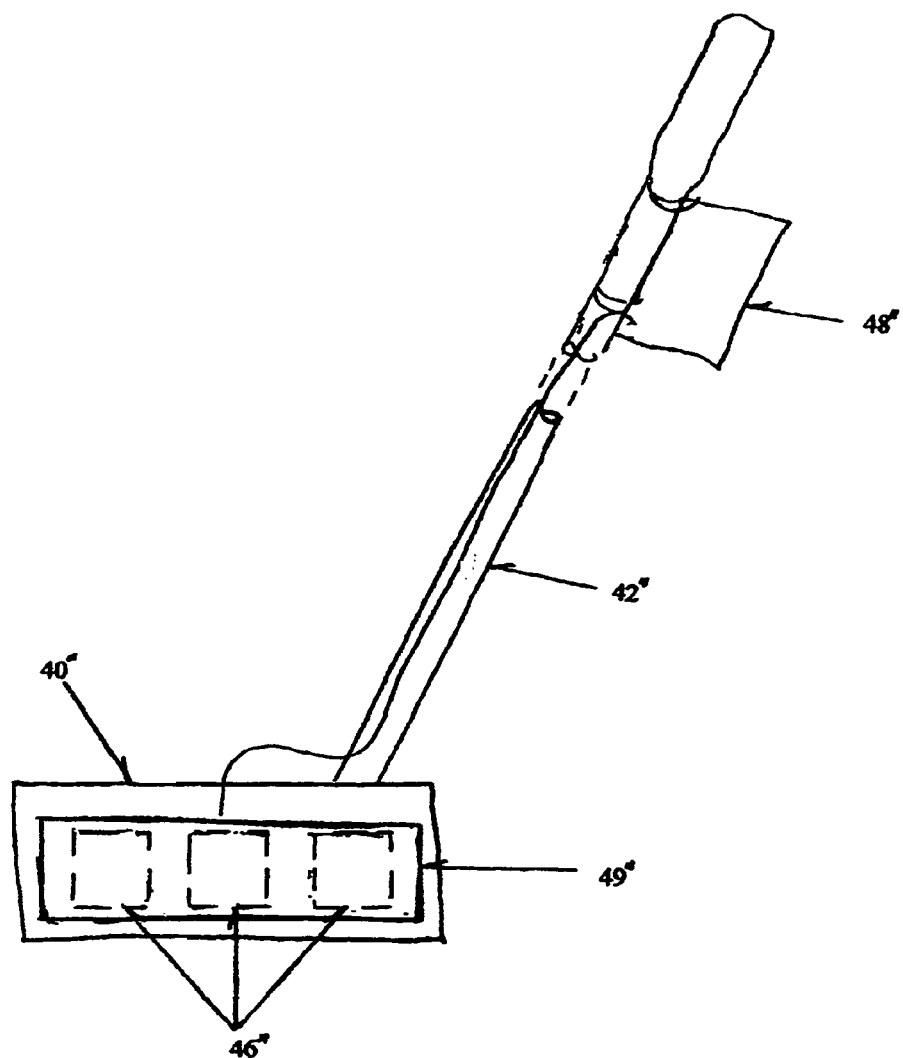
FIGURE: 4

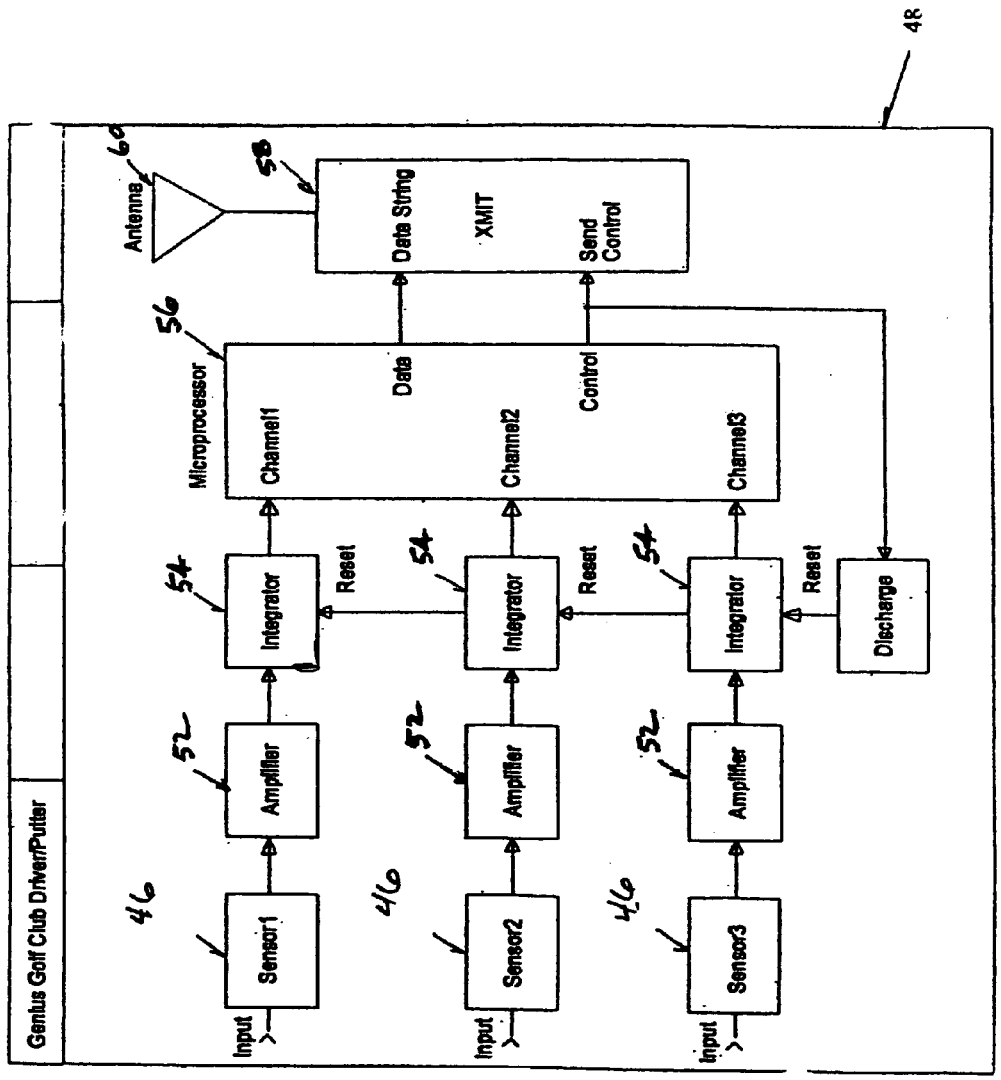
FIGURE: 5

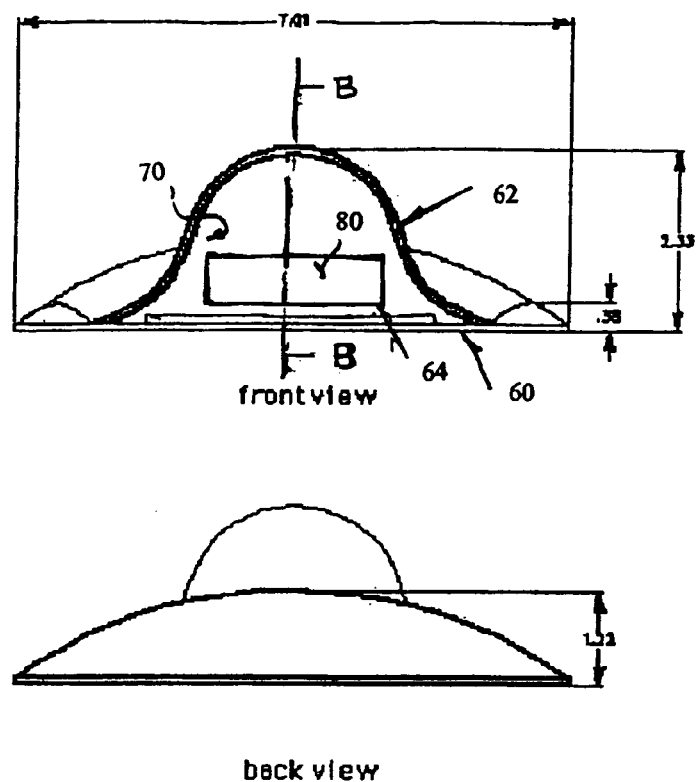
FIGURE: 6A

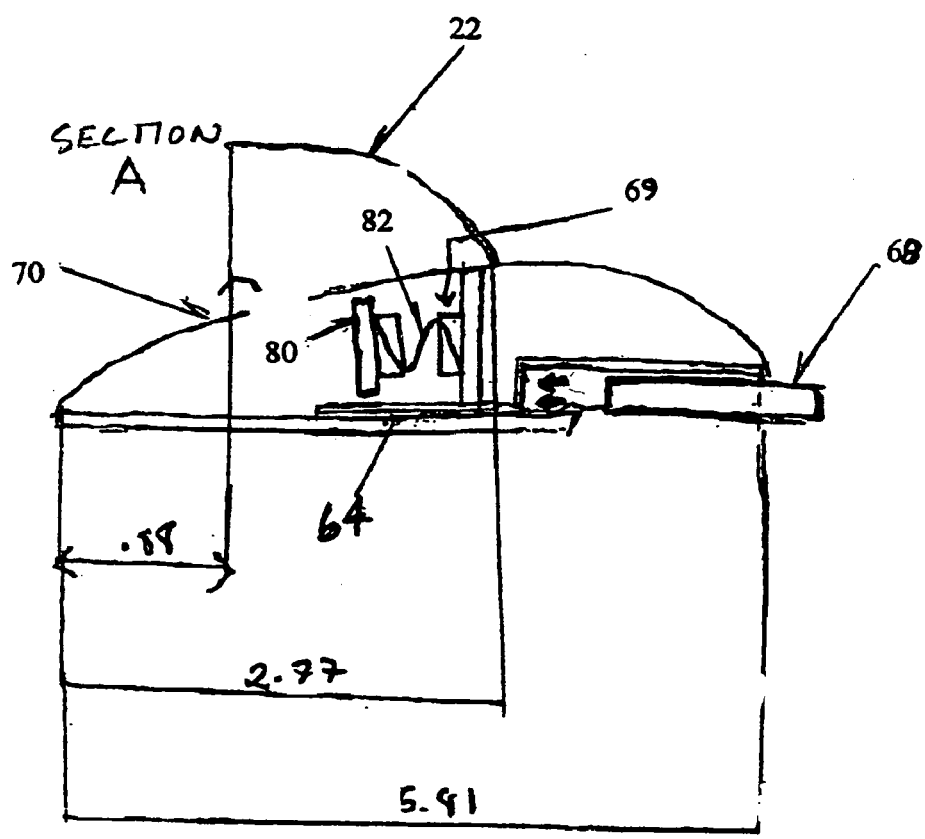
FIGURE: 6B

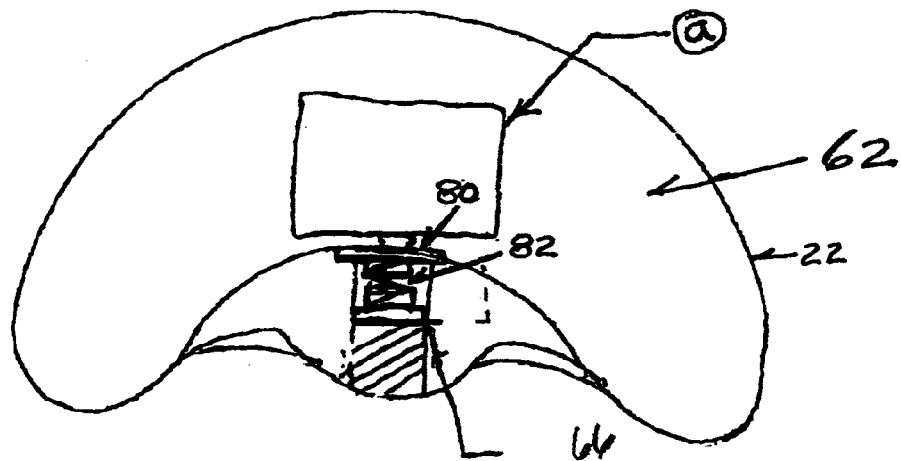
TOP VIEW WITH COMPONENTS exposed
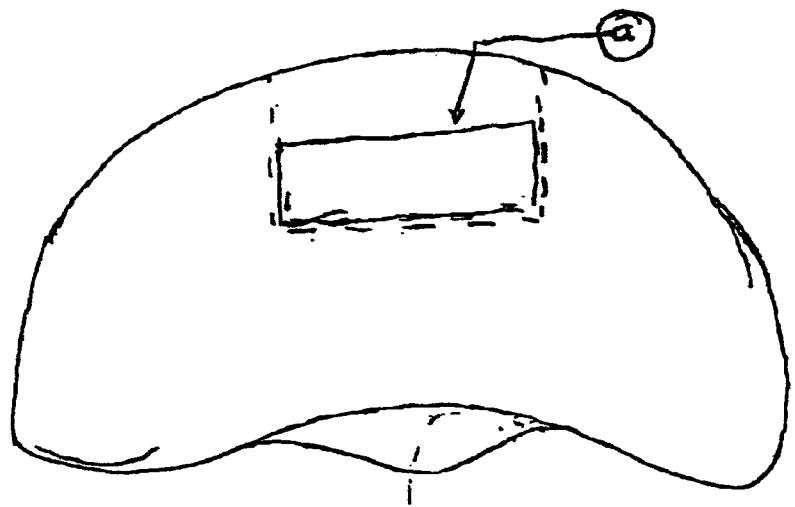
(a) Bottom view with eletronics in position
FIGURE: 6C

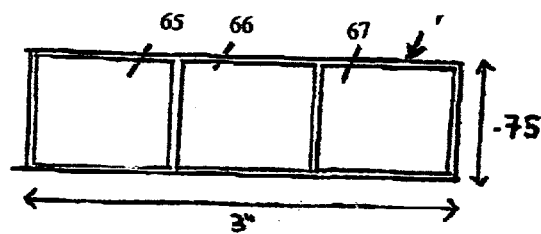
Tripad Sensor with three different activation areas
FIGURE: 7

FIGURE: 10

Visual Gaming Software Process Flow Diagram
Confidential

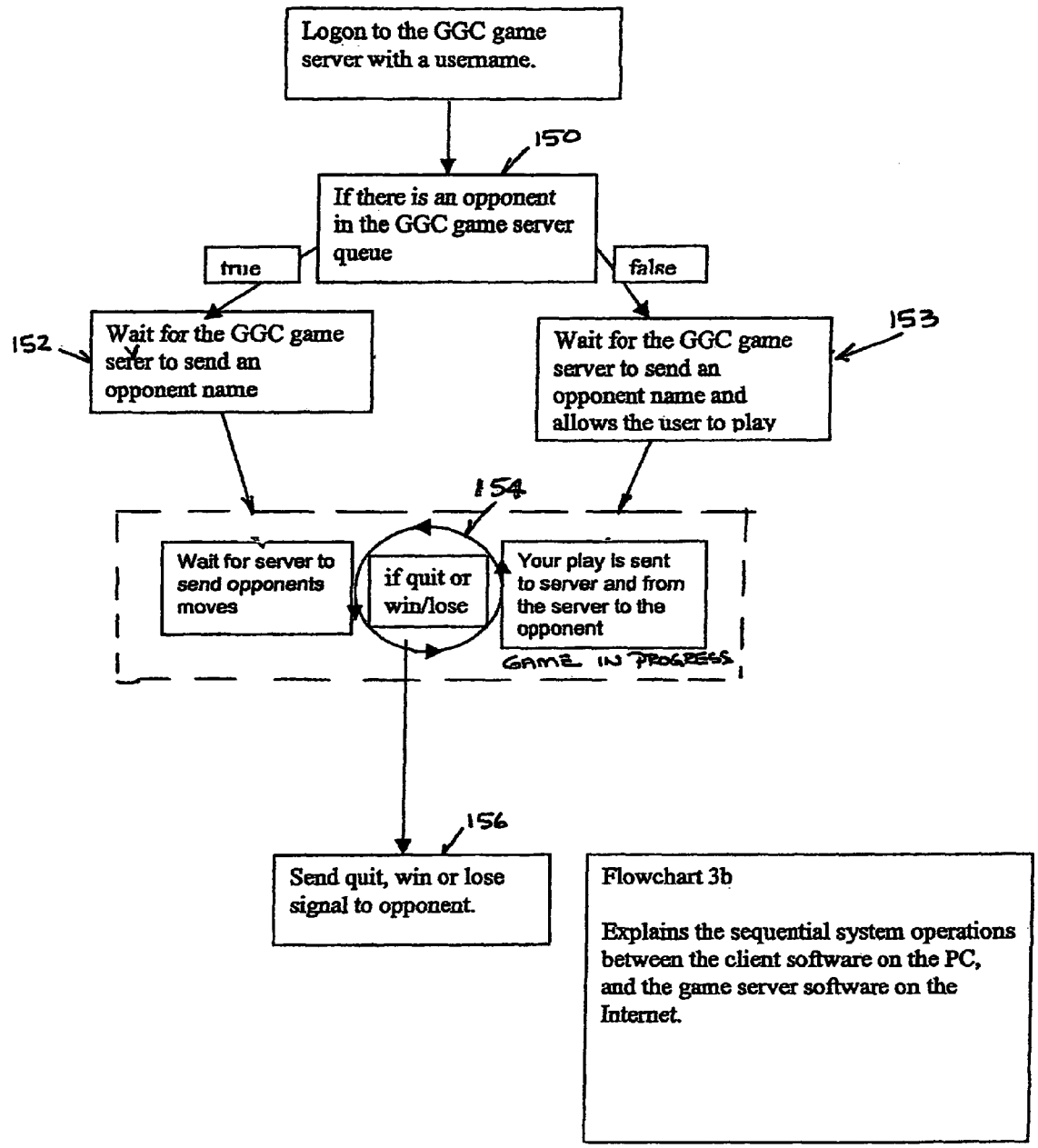
FIGURE: 12

SMART GOLF CLUB MULTIPLAYER SYSTEM FOR THE INTERNET

CROSS-REFERENCE TO RELATED APPLICATION

Priority is claimed from U.S. Provisional Application Ser. No. 60/133,722, filed May 12, 1999 for all subject matter common hereto. That provisional application is incorporated by reference herein.

REFERENCE TO MICROFICHE APPENDIX

A microfiche appendix including 1 microfiche with 27 frames accompanies and forms a part of this application.

FIELD OF THE INVENTION

This invention relates to a system coupling actual sporting equipment and a computer. More particularly, the invention relates to a system wherein a golf club, a golf club swing detector and/or a golf ball receptacle communicate wirelessly to a personal computer and thereby, if desired, to the interne.

BACKGROUND OF THE INVENTION

A number of patented golf club devices embody various ball contact or club swing sensing components. Typically, these devices display information related to a golf player's swing and accuracy in hitting a golf ball. In certain of these, the information is displayed or signaled by some part of the golf club itself in the form of a small visual readout or an audible sound. One such device contains an array of mechanically depressible pins on the face of the golf club. When the ball is struck by the club, the pins are physically depressed in a pattern to inform the player of the location on the club face where contact with the ball occurred. Another device uses a light emission and reflection detection technique to provide a player information, displayed on the club, regarding the alignment of the golf ball with the preferred location on the golf club face.

Also, numerous conventional computer golf game software packages and video games use a variety of unrealistic techniques to emulate the striking of a golf ball with a club. None of these cooperates with actual golf clubs, actual golf ball target or cup receptacles, or a swing detector that senses the actual golf stroke.

It is desirable to remotely communicate actual player performance information, whereby more sophisticated analysis and prediction possibilities are realizable via computer technology and state of the art display techniques. Further, it is also desirable to use such performance information in an expanded capacity to provide interactive competitive play among numerous players in locations remote from each other.

SUMMARY OF INVENTION

This invention relates to a system that interconnects real golf or other sports equipment to a computer. In a preferred embodiment the computer is coupled wirelessly to a golf club, a receptacle or a club swing sensing component. Further, the invention, with the components summarized below, allows one or more golfers to enter into a competition against each other. Each player asks the computer who is available to play a contest. Once a player pairs up against another player anywhere in the world and play ensues, the computer and display show each participant's score via animation or graphics that preferably relate to a player's individual performance statistics. A single player may play without an opponent to practice and improve basic golfing skills using the computer and display to track performance.

The system application is unlimited. Much of this system can be used not only for golfing competition on the Internet, but for other sports as well. Sports implements other than golf clubs, swing detectors and receptacles can be outfitted with sensors according to this invention and used for training purposes, rehab, or for interactive internet competition.

The technology can be used for training, competition, and the improvement of player reflexes and coordination. With little or no modification, the technology also has applications in medicine, particularly physical therapy.

1. Smart Golf Club.

A wireless golf club is constructed to contain or alternatively, a standard golf club is modified to contain, a multiple sensor or transducer array located on the club head at the head face or hitting surface. Upon impact of the head of the club with a golf ball, the impacted sensors produce detectable variances representing the magnitude and duration of the club-ball impact force and the proximate location of such contact relative to the preferred location, the "sweet spot", on the face of the club head. The variances are electronically processed into digitally coded information and remotely transmitted by an electrical communication circuit either contained within or attached to the golf club.

2. Golf Ball Receptacle.

A ball receptacle has an open end to receive a golf ball and contains a transducer located so as to sense the ball entering receptacle. Upon impact with the golf ball, the sensor produces a detectable variance representing impact with the ball. The variance is electronically processed into digitally coded information and remotely transmitted by an electrical communication circuit. In one preferred embodiment the communication circuit is contained within the receptacle. Preferably the communication circuit for the receptacle is a radio frequency transmitter. The receptacle can either be designed for indoor use or can be a cup in an actual green with the communication circuit housed in the cup or elsewhere.

In each of the golf club device and golf ball receptacle device according to this invention, in a preferred embodiment the transducers are or include piezoactive elements. As used herein, "piezoactive" includes piezoelectric and piezoresistive components. Piezoactive components are defined as components the electrical properties of which, when the component is subjected to physical force, vary.

3. Golf Club Motion Sensor Plate.

A golf club swing motion sensing device contains an array of uniformly distributed sensing transducers upon or proximate to the device surface. This motion sensing device may be formed as a mat or a plate or other substantially flat surface from which a golf ball is hit. The transducers produce detectable varying characteristics such as capacitance representing the velocity, angle, and proximity of a golf club relative to the surface of the device. The variances are electronically processed into digitally coded information and remotely transmitted by an electrical communication circuit contained within or electronically connected to the device.

4. Wireless Signal Receiver and Computer.

At each remote player site, wireless radio frequency equipment receives the digitally coded transmitted signals from the golf club, the golf ball receptacle, and the club swing motion sensing device. The signals are demodulated and processed into serial binary data suitable for communications to the computer via either serial or parallel ports. As the game progresses, the computer under the control of the golfing software, monitors and directs the flow of communications between the players via the internet and displays the game simulations and performance information.

5. Computer Golfing Software System.

At each remote player site, a computer under the control of the golfing software program, monitors and controls the sequential play of the game and interacts with the player at the site and also competing players at other remote sites via the internet. The software system generates the game simulations for display and tracks each player's performance as the game progresses.

The above and further features and advantages of the invention will be better understood with reference to the accompanying drawings and the following detailed description of preferred embodiment.

BRIEF DESCRIPTION OF THE DRAWINGS

FIG. 1 is a diagrammatic illustration of components of a computer implemented golf system according to this invention.

FIG. 2 is a top plan view of a golf club head with sensors and circuitry and used in the computer implemented system of FIG. 1.

FIG. 3 is a front elevation view of the golf club head of FIG. 2 and shows three sensors located at the face of the club head.

FIG. 3A is a front plan view of a further embodiment of a club head for use with the computer implemented golf system of FIG. 1.

FIG. 4 is a diagrammatic front plan view of a putter with a club head and circuitry forming a further, alternative embodiment of a club for use with the computer implemented system of FIG. 1.

FIG. 5 is a schematic block diagram of a club head electronics installation for use with the club heads of FIGS. 2-4.

FIG. 6A is a front elevational view of a golf ball receptacle for use with the system of FIG. 1.

FIG. 6B is a cross-sectional view along the lines B-B of FIG. 6A.

FIG. 6C is a fragmentary top plan view of the receptacle of FIGS. 6A and 6B illustrating internal components of the receptacle.

FIG. 7 is a top plan view of a golf ball sensing element with three distinct activation areas for use in the receptacle of FIGS. 6A-6C.

FIG. 12 is a block diagram illustrative of a portion of the operation of the computer of FIG. 10 operating as indicated in the flowchart of FIG. 11.

DETAILED DESCRIPTION OF PREFERRED EMBODIMENT

Figure 8:
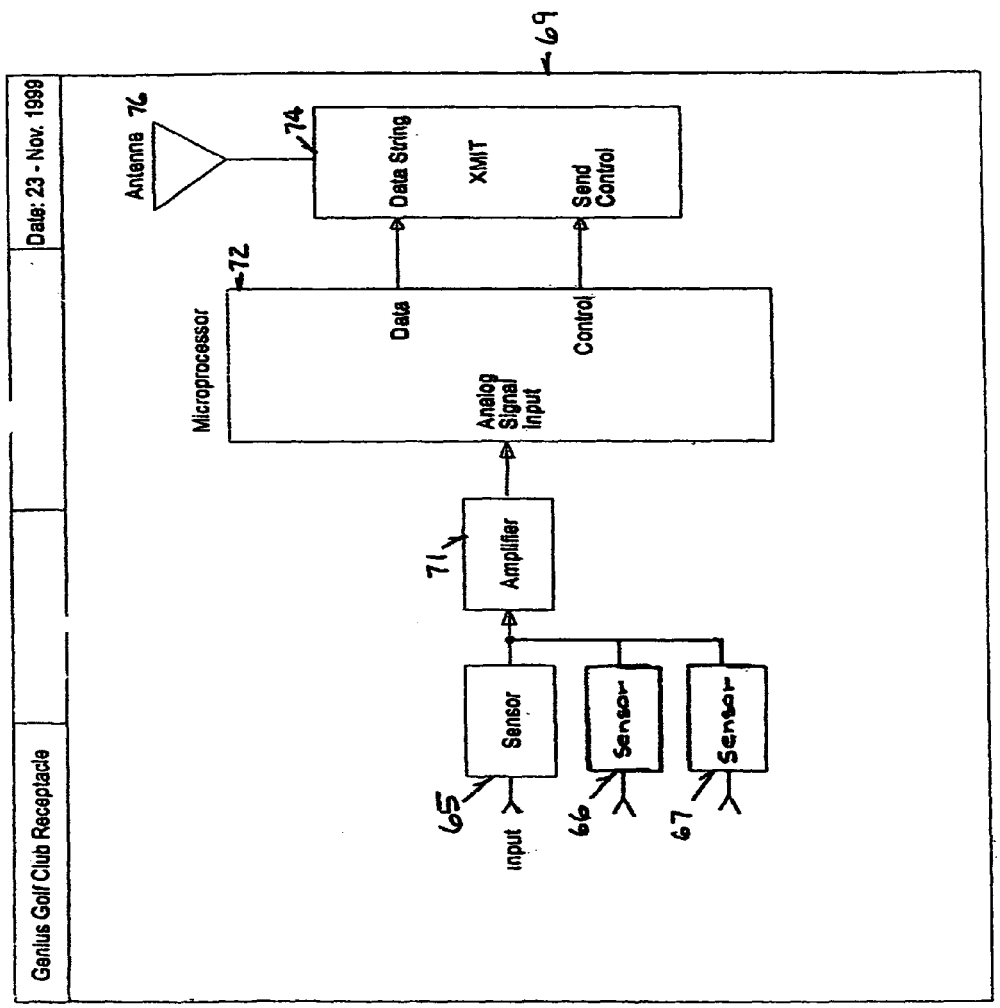
FIG. 8 is a schematic block diagram of a receptacle electronics installation for communicating with the computer in a computer implemented system according to FIG. 1.
Figure 9:
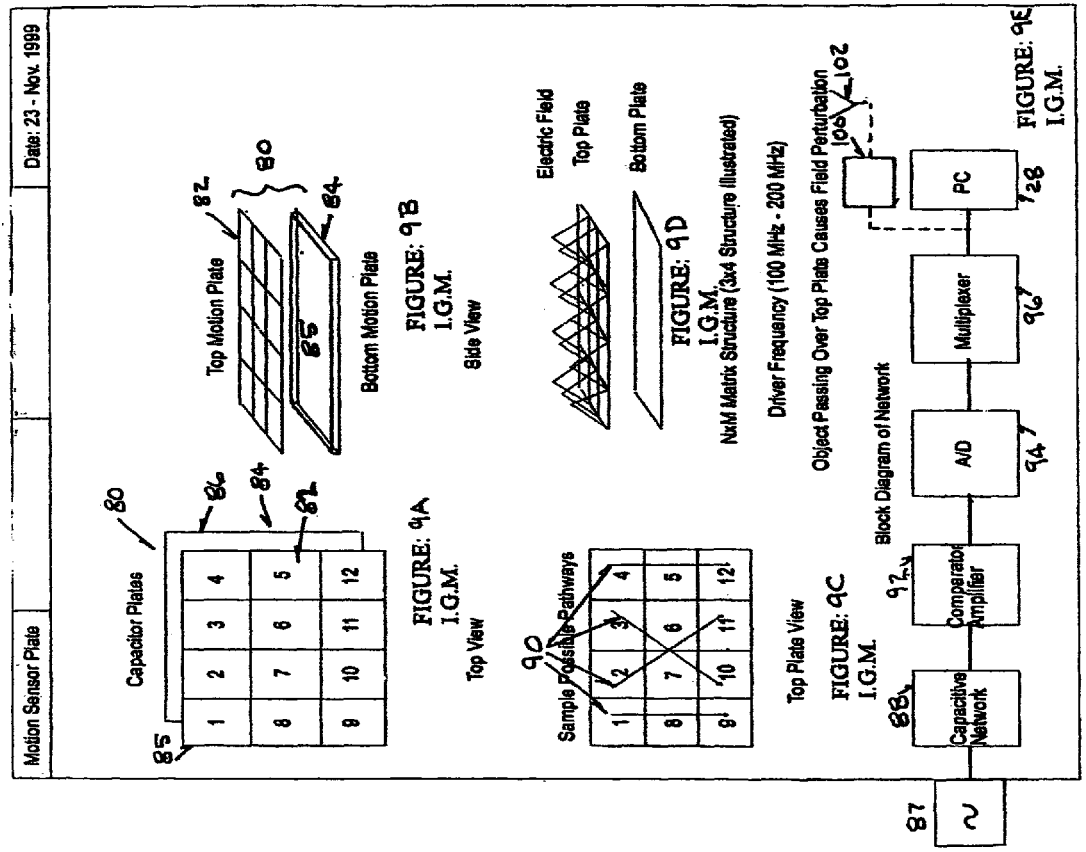
FIGS. 9A-9D are diagrammatic illustrations of a golf club motion or swing sensor plate for use with the system according to FIG. 1.
FIG. 9E is a block diagram of electronics used in association with the swing sensor plate of FIGS. 9A-9D.

As shown in FIG. 1, a preferred embodiment of the invention includes a wireless smart golf club 20, a wireless golf ball receptacle 22, a wireless golf club motion sensing plate 24, a wireless receiver 26 connected to a computer 28, and a display or monitor 30 with speakers 31 operated under the control of golf system software 32, and connected via the internet to an internet golf game server 34 (called herein the GGC server).

1. Smart Golf Club

The smart golf club 20 has a head 40 and a shaft 42. As shown in FIGS. 2 and 3, the head 40 has a shaft opening 42, a plurality of embedded contact sensors 46 (three are illustrated in the preferred embodiment), and internal electronic circuitry 48 including a wireless radio frequency transmitter (58 in FIG. 5). As shown, at least one of the sensors 46 is located at or proximate to the optimal location on a club face 47 for contact with the golf ball, the "sweet spot" 49. The remaining two sensors are adjacent and on either side of the sweet spot 49. The contact sensors may be, but are not limited to, sensors employing piezo-active type transducers, specifically, either piezo-electric or piezo-resistive transducers (similar, but not limited to the Cooper Instruments LPM 562).

In an alternative embodiment, FIG. 3A, three sensors 46' are applied to the face of an adapted club by a mylar tape or other means 49. Again, the electronic circuitry is internal to the club head 40' and connects to the sensors 46' by leads 27.

In a second alternative embodiment, to retrofit a standard golf club, contact sensors 46" are part of an adapter 40" attached to an ordinary club head as seen in FIG. 4 and wire connected to electronic circuitry 48" attached to the club shaft 42" or elsewhere on the club.

A golf ball contacting any sensor 46 produces a detectable variance indicating the magnitude and duration of sensor-ball impact. The variance may be a change in resistance of a piezo-resistive transducer or a voltage change in the case of a piezo-electric transducer. As shown in FIG. 5, the variance is detected and amplified by an associated amplifier 52 and then is input to an associated integration circuit 54, the output of which represents the energy of the ball-club contact event. Connected to the integration circuit 54, a microprocessor 56 is a multi-input channel signal processing circuit (similar, but not limited to a Motorola #68HC05) having analog to digital signal converting circuits (ADCs), one for each input channel, and a sequential digital signal encoding circuit connected so as to convert the ADC outputs into a time multiplexed serial digital data stream containing a binary coded word for each channel indicating the energy of the associated sensor-ball impact event.

A radio frequency transmitting circuit 58 receives the serial digital data from the microprocessor 56 and wirelessly transmits the information via an internal antenna 60 to the receiver 26 (FIG. 1) for subsequent processing by the computer 28.

2. Golf Ball Receptacle

The golf ball receptacle 22 has a top 62 shaped to allow entry of a golf ball, as shown in FIGS. 6A, 6B and 6C. The receptacle has a contact sensor pad 64, shown in FIG. 7, containing at least one contact sensor (three different activation areas 65, 66 and 67 are illustrated in the preferred embodiment), a ball return mechanism 69 (FIG. 6B), and internal electronic circuitry 68 (FIG. 6B). The internal circuitry includes a wireless radio frequency transmitter (not separately shown in FIGS. 6A, B and C). As shown, the preferred embodiment has contact sensor pad 64 positioned within the receptacle 60 such that the center activation area 66 aligns with the center of a ball entry 70. Additional sensor activation areas 65 and 67 are adjacent, one on either side of the center area 66. In the preferred embodiment, of FIGS. 6A, 6B and 6C, and like the sensor used at the face of the club, the sensors may be, but are not limited to, sensors employing piezo-active type transducers, specifically, either piezo-electric or piezo-resistive transducers.

A golf ball entering the receptacle 60 and contacting the sensor pad 65, 66 or 67 produces a detectable variance indicating the ball entry event. The variance may be a change in resistance in the case of a piezo-resistive transducer (similar, but not limited to Cooper Instruments LPM 562) or a voltage change in the case of a piezo-electric transducer. As illustrated in FIG. 8, the variance is detected and amplified by an associated amplifier 71. This amplified signal then is input to a microprocessor 72 having an analog to digital signal converting circuit (ADC) and a digital signal encoding circuit connected so as to convert the ADC output representing the sensors' signals into a serial digital data stream containing a binary coded word indicating the sensor-ball contact event. The microprocessor 72 may be the same or similar to the microprocessor 56 of the golf club electronics. A radio frequency transmitter circuit 74 receives the serial digital data from the microprocessor 72 and wirelessly transmits the information via an internal antenna 76 to the receiver 26 (FIG. 1) for subsequent processing by the computer 28.

The ball return mechanism 68 can be as simple as a back plate 80 located to be engaged by a golf ball entering the receptacle 22 and supported and biased by a spring or springs 82 to eject the ball. Other known ejection devices, similar to those used in pin ball machines, and either mechanically or even electrically activated, can be used to improve the effect if desired.

The receptacle configuration is susceptible to much variation. The receptacle illustrated and described above is well suited to indoor use, on carpet for example. It is clear, however, that an actual cup, installed in an actual green, with real or synthetic grass, can be similarly equipped.

3. Golf Club Motion Sensor Plate.

The golf club motion sensor plate 80 having a top motion plate 82 and a bottom motion plate 84 is diagrammatically shown in FIGS. 9A-D, wherein the top motion plate 82 contains a plurality of capacitor-forming electrically isolated platelets 83 (twelve platelets are illustrated in this exemplary preferred embodiment). They are evenly distributed at or just below the top plate's exterior upper surface 82. The bottom plate 84 has a homogenous electrically conductive interior surface 85 underlying the platelets 83. Each capacitive platelet 83 contained in the top motion plate 82 forms a capacitive component when the top and bottom motion plates are vertically closely spaced to form the golf club motion sensor plate. A suitable insulator may be sandwiched between the two plates. The structure is adhesively or otherwise mechanically joined and it may be covered or coated as desired. The result is a golf club motion sensor plate 80 containing a capacitor matrix (a 3×4 capacitor matrix is illustrated in the preferred embodiment). The capacitive components 83 are connected to form a capacitive network 88 as is indicated in FIG. 9E.

Applying an energizing high frequency alternating electrical signal having a frequency in the range from 100 MHz to 200 MHz from an oscillator 87 to the golf club motion plate capacitive network 88 produces a electromagnetic field above the surface of each platelet 83 of the capacitive components of the motion sensor plate 80. Any object, including a golf club, passing near the surface of the energized motion plate will cause a perturbation of the electromagnetic field as illustrated by the sample possible pathways 90 across the plate in FIG. 9C. A network 92 of electrical comparator amplifiers (FIG. 9B) is connected to the capacitor network. The comparator amplifiers of network 92 are connected one to one with the capacitive elements of the capacitive network 88. The comparators of the network 88 detect voltage variations occasioned by electromagnetic field disturbance due to a golf club moving over certain of the capacitive elements of the motion plate. Each different golf club motion over the energized motion plate will produce a uniquely identifiable signal from the comparator amplifier network. There are a variety of known proximity sensors that could be gathered together in an array like that of the platelets 83 to serve as the transducer portion of the golf club motion detector.

The electrical signal from the comparative amplifier network 92 is applied to an analog to digital signal converter 94 (ADC) and the ADC digitized output signal is converted into a serial digital data stream by a multiplexer 96. This data identifies each platelet having had its field distrubed. The serial digital data can be input directly by wire from a multiplexer 96 to the computer 28 located at the site of the golf player and golf club motion sensor plate 80, or as in the preferred embodiment, illustrated in FIG. 1, the serial data can be transmitted to a remotely located receiver 26 connected to the computer 28 via a transmitter 100 and an antenna 102 included in the golf club motion electronic transmitter communication circuitry from FIG. 1.

The computer 28, under the control of the golf system software, will analyze the serial digital club motion signal, recognize from the transmitted signals the platelets 83 over which the club head passed and display the golf club swing motion.

4. Wireless Signal Receiver and Computer.

Figure 10:
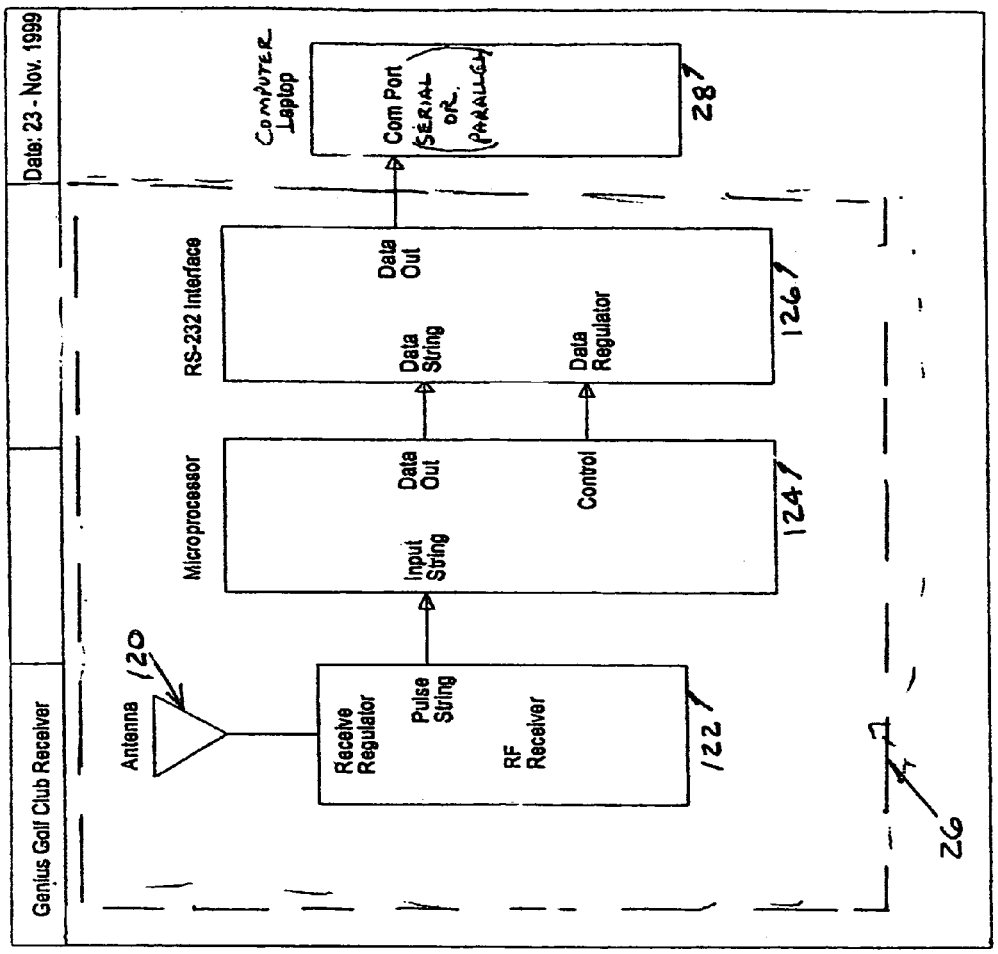
FIG. 10 is a block diagram of a computer installation for use as the computer and information receiving interconnect of the system of FIG. 1.

At each player site, a wireless radio frequency signal receiver 26 is connected to the computer 28 by either the serial (USB) or parallel computer ports, as shown in the functional block diagram, FIG. 10. The wireless signal receiver 26 detects digitally coded radio frequency transmissions from the communication circuit associated with any of a smart golf club 20, a golf ball receptacle 22, or a golf club motion sensing plate 24, as shown in FIG. 1. The received transmissions are demodulated by the RF receiver circuitry 122 (FIG. 10) connected to a microprocessor 124, which converts the demodulated data signal to serial binary coded data suitable for communications to a computer 28. The computer 28, under the control of the internally installed golf system software program, monitors and directs the flow of communications between remotely located players via the internet and displays the game simulations and performance information. In appropriate installations the wireless electromagnetic signals that communicate with the receiver may be infrared communications.

5. Computer Golfing Software System

Figure 11:
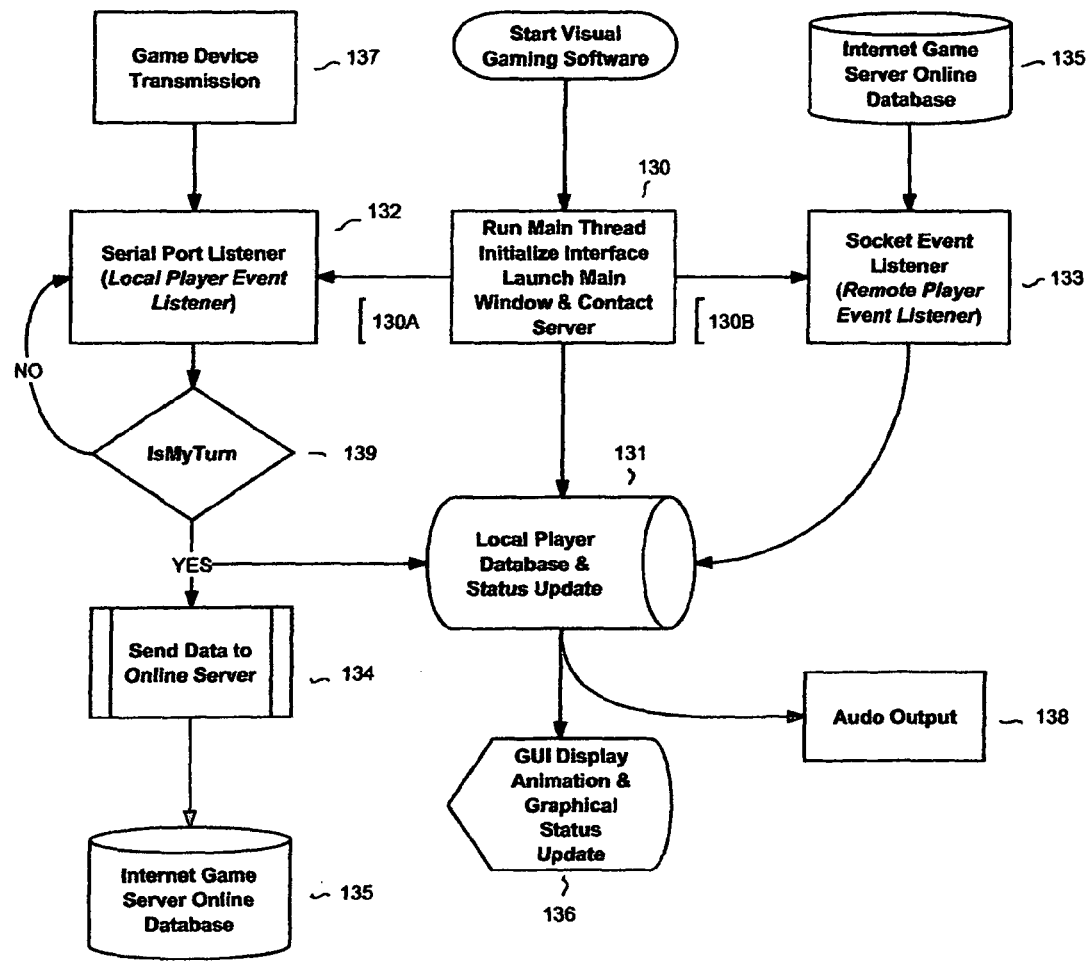
FIG. 11 is a functional flowchart of the software operation of the computer of FIG. 10.

At each remote player site, the computer 28 (FIG. 1) under the control of the golfing software system program (shown in the golfing software system functional block diagram, FIG. 11) monitors and controls initialization and the sequential play of the golf game, or alternatively, the individual player practice session. Upon start up by a player at a particular site, the system input parameters are set and the system internet and player data port interfaces are initialized 130 as indicated by the arrows 130a and 130b. For internet communications, the serial port of the computer 28 is enabled in the preferred embodiment. A local player event listener is initialized. It will communicate events from one or more of the smart golf club, the golf ball receptacle and the motion sensor plate. The main operational software (program) thread is run 130, and the system awaits data input from the appropriate computer communications port at 132, 133.

If the competitive play mode has been selected, the program generates a player participation request and sends 134 the request to the GGC game internet server (GGC server) 34 (FIG. 1). Upon identification of a player opponent at 150

(FIG. 12) by the GGC server, the program initiates the player identification sequence 152 and sequential play begins 154. This software sequence and control routine occurs at each remote site where play has been initiated. During the game play sequences 154, the program generates the appropriate animation, display, and audio data and commands 136 and 138 (FIG. 11), and communicates with the associated display and speaker devices 30 and 31 (FIG. 1). Upon the occurrence of a local player event, detected at 132, the main operating program at 130, displays the event at 136, and communicates the event at 133 by causing a device transmission at 137 to be sent at 134 via the internet GGC server 135 which displays the event for the opposing players and alerts an opposing player that it is his/her turn to play. The local player event may be, but is not limited to the smart golf club impacting a ball, the swing of a club across the sensing plate or the balls entry into the receptacle. The program contains time delay limits for player action, and delays of play beyond these limits generate play quit and disconnect signals.

The event at 132 also has the effect of indicating at 139 that it is no longer the local player's turn and enables (as indicated by line 139') the socket event listener at 133 to detect an event from the remote player, again via the internet.

If the single player practice mode is selected, the internet communications sequences are disabled, other software sequential operating routines continue as above described and the player's golf club stroke, ball-receptacle contact, and/or club swing motion sensor information are communicated only to the computer located at the player's site and the performance information analyzed and displayed only at the local player's site.

When a game is won, lost, or terminated, the golf software system generates the appropriate output signals 156 (FIG. 12), displays the player performance information, and resets to initial pre-game conditions. If one player opponent quits the game or is "timed out" (due to excessive delay in play) and the remaining player wishes to continue play, the software resumes an internet search for another opponent 152 and 153.

Using programming as contained in the accompanying microfiche appendix, one skilled in the art can readily accomplish the game programming described. Alternative programming too will be apparent from the foregoing functional description and the illustrations contained in the appended drawings.

While a preferred embodiment has been described, it will be appreciated that many variations and modifications in the system, its operation, and its various components may be made without departure from the spirit and scope of invention as set forth in the appended claims.

What is claimed is:

1. A computerized interactive sports system comprising:
   At least two remote player sites comprising:
   A golf club comprising a grip, a shaft, and a club-head;
   A first array of sensors mounted on the face side of said club-head of said golf club;
   A second array of sensors comprising one or more contact sensors mounted to a target receptacle;
   A third array of sensors comprising golf club motion sensing devices attached to and or static and detached from said golf club;
   A first computer programmed to process data derived from data acquired by said first, said second, and said third sensor arrays;
   A first communications link for transmitting data derived from said data acquired by said first sensor array to said first computer;
   A second communications link for transmitting data derived from said data acquired by said second remote sensors to said first computer; and
   A display monitor connected to said first computer;
   A second computer programmed to communicate with said at least two remote player sites;
   A third communications link for transmitting data derived from said data acquired by said first computers to said second computer; and
   A fourth communications link or medium for transmitting data derived from said data acquired by said second computer to at least one of said first computers;
   Wherein said first computer is further programmed to analyze the performance of a person swinging said golf club so that said club-head strikes a golf ball with said performance analysis being based on said derived data transmitted by said first and second communications links; and to further control said display monitor to display the results of said performance analysis;
   Wherein said second computer is programmed to cause the transfer of local player events from a remote player site to another remote player site for presentation to another player, notify players when it is their respective turn to play, measure player time delays, disconnect player remote sites with excessive time delays, and conduct an Internet search for another opponent if the remaining player wishes to continue play.

2. The computerized interactive sports system as recited in claim 1, wherein said first computer is further programmed to send the results of said performance analysis to said second computer upon completion of said performance analysis via said third communications link.

3. The computerized interactive sports system as recited in claim 1, wherein said third sensor comprises motion sensing devices or a motion detector mounted internally or externally to said golf club or a sports implement.

4. The interactive sports system as recited in claim 3, wherein said spatial orientation devices further comprise the following:
   An infrared device attached to said golf club, gaming tool, or sports implement; and
   An array of infrared receivers attached to said target receptacle unit.

5. The computerized interactive sports system as recited in claim 1, wherein said first sensor array comprises piezoactive transducers, pressure, and or force sensors.

6. The computerized interactive sports system as recited in claim 1, further comprising electronic circuitry for outputting to said first communications link a signal representing the energy and momentum of a ball-club contact event derived from data acquired by said first sensor array.

7. The interactive sports system as recited in claim 6, wherein said electronic circuitry comprises a computing device mounted to said golf club, sports implement, or gaming device, and said target receptacle, programmed to convert data acquired by said first, second, and third sensor arrays into a time-multiplexed serial digital data stream containing a respective binary coded word for each channel.

8. The computerized interactive sports system as recited in claim 1, wherein said third sensor array further comprise an array of capacitors, and said golf club motion sensing device further comprises a high frequency oscillator coupled to said capacitor array for detecting the motion of a standard golf club or sports implement.

9. The interactive sports system as recited in claim 8, further comprising:

A network of comparator amplifiers respectively connected to said capacitors for detecting voltage variations occasioned by disturbance due to proximal motion of said golf club;

An analog-to-digital converter for converting the analog outputs of said comparator amplifiers into digital signals; and A multiplexer for converting the parallel digital signals into a serial digital data stream that is received by said first computer; and A transmitter for wireless communication with said first computer.

10. The interactive sports system as recited in claim 9, wherein said computer is further programmed to analyze the serial data stream, identify the capacitors that experienced a disturbance due to the proximal motion of a standard golf club; and control said display monitor to display the golf club motion as a function of the identified capacitors.

11. The computerized interactive sports system as recited in claim 1, wherein said second computer comprises a sports competition server connected to said first computer via a network, which comprises the fourth communications link, wherein said first computer is further programmed to process data from said sports competition server representing the user performance of a competition at a remote site during the turn of said competitor;

wherein said sports competition server selects remote players from a queue of awaiting players in response to a first player indicating a readiness to play.

12. The interactive sports system as recited in claim 11, wherein said sports competition server is programmed to establish connections amongst subscribing players at a plurality of remote locations via said network.

13. The interactive sports system as recited in claim 11, wherein said second computer is further programmed to create and manage a plurality of games and players wherein said games comprise one or more said first computers of opponents connected to said first computer;

Wherein each first computer comprises a network port for connecting to said network, a serial data port for receiving a serial data stream from a respective set of sensors designed to detect the motion of respective sports equipment items or controllers being manipulated by a respective player and a port for connecting to its respective display monitor where each first computer is programmed to perform the following:

Processing the digital data stream from said respective set of sensors into game data having a format representing game results for said first computer player; controlling the respective display monitor to provide visual feedback concerning the progress of the game;

Transmitting said game data from said first computer player to said second computer that comprises said sports competition server; and Polling said competition server for receipt of game data and or messages from opponents or players at remote sites.

14. The interactive sports game system as recited in claim 13, further includes electronic sports equipment comprising an electronic golf club or standard golf club retrofitted with electronic devices operably connected to said first computer and said sports competition server via a network, and the impacted object is a projectile such as a golf ball.

15. The computerized interactive sports system as recited in claim 1, wherein said first computer programming comprises:

A serial port listener software program that receives acquired data from said first, second, and third sensor arrays;

a socket event listener that receives data from said sports competition server; and A main thread for alternately processing data received by either said socket event listener or said serial port listener in accordance with sports competition format wherein acquired data from said first, said second, and said third sensor arrays are processed by said first computer and the results are sent to said sports competition server only if data has been previously received from said sports competition server indicating that it is that player's turn to play, otherwise, acquired data from said golf club, said golf club motion sensing devices, and said target receptacle are ignored by said computer if data has been previously received from said sports competition server indicating that it is a remote player's turn to play;

Wherein controlling the reception of data received from said first, said second, and said third sensor arrays is allowed only on that player's turn thus allowing sequential play, the use of one or more said golf clubs, one or more said golf club spatial orientation and directional devices, and one or more target receptacles with one or more said first computers in the network.

16. The computerized interactive sports system as recited in claim 1, wherein said computer programming further comprises single-player sports training software for providing training as a function of the data received from said golf club, said golf club motion sensing device, and said target receptacle.

17. The computerized interactive sports system as recited in claim 1, wherein said first computer further comprises audible golf image simulation and display software for displaying images that simulate the results of said performance and analysis.

18. The computerized interactive sports system as recited in claim 1 comprising:

A row of sensors mounted on said face of said club-head of said golf club for acquiring data from respective channels, and said acquired data representing the force, time of contact, energy, and position of the impact of a golf ball relative to each impacted sensor when a golf ball is struck by said club-head;

A target receptacle comprising at least one contact sensor for acquiring data representing the struck ball or object entering the target receptacle;

An accelerometer attached to said golf club, gaming tool, or sports implement to detect spatial translational motion and or rotational orientation of said golf club, gaming tool, or sports implement;

A first computer having a data input port for receiving data and an output port for communicating with said display monitor of said first computer;

A first communications link for communicating data derived from said impact data acquired by said row of sensors in said respective channels to said data input port; and A second communications link for transmitting data derived from impact data acquired by said contact sensor of said target receptacle to said data input port;

Wherein said first computer is programmed to process said received data into data representing the final location of the struck ball relative to a target receptacle, and control said display monitor to display animated feedback having visual indicators representing the trajectory and final location of the golf ball relative to said target receptacle, except if the impact data from the contact sensor of said target receptacle indicates that the ball entered said target receptacle.

19. The computerized interactive sports system as recited in claim 1, wherein said first communications link comprises a telemetry system and comprises a wireless transmitter housed inside or attached to said golf club and a wireless receiver coupled to an input port of said first computer as said first communications link to said first computer.

20. The computerized interactive sports system as recited in claim 1, wherein said second communications link further comprises a wireless transmitter mounted inside said target receptacle and a wireless receiver coupled to an input port of said first computer as said second communications link to said first computer.

* * * * *